United States Patent [19]

Jeschke et al.

[11] Patent Number: 5,428,047

[45] Date of Patent: Jun. 27, 1995

[54] USE OF SUBSTITUTED 1,2,4-OXADIAZOLE DERIVATIVES FOR COMBATING ENDOPARASITES, NEW SUBSTITUTED 1,2,4-OXADIAZOLE DERIVATIVES, AND PROCESSES FOR THEIR PREPARATION

[75] Inventors: Peter Jeschke, Levekusen; Werner Lindner; Achim Harder, both of Cologne; Norbert Mencke, Levekusen, all of Germany

[73] Assignee: Bayer Aktiengesellschaft, Leverkusen, Germany

[21] Appl. No.: 124,909

[22] Filed: Sep. 21, 1993

[30] Foreign Application Priority Data

Sep. 28, 1992 [DE] Germany ............ 42 32 418.1

[51] Int. Cl.$^6$ .................. C07D 271/06; A61K 31/41
[52] U.S. Cl. .................. 514/364; 548/131; 546/277
[58] Field of Search ................ 548/131; 514/364

[56] References Cited

U.S. PATENT DOCUMENTS

| | | |
|---|---|---|
| 3,879,407 | 4/1975 | Hagarty . |
| 4,012,377 | 3/1977 | Claisse et al. . |
| 4,294,842 | 10/1981 | Weston . |
| 4,294,843 | 10/1981 | Weston . |
| 4,488,895 | 12/1984 | Stetler ............... 548/131 |

FOREIGN PATENT DOCUMENTS

| | | |
|---|---|---|
| 8356 | 7/1979 | European Pat. Off. . |
| 7529 | 9/1979 | European Pat. Off. . |
| 10163 | 9/1979 | European Pat. Off. . |
| 492249 | 12/1981 | European Pat. Off. . |
| 92706 | 4/1983 | European Pat. Off. . |
| 245818 | 5/1987 | European Pat. Off. . |
| 337151 | 3/1989 | European Pat. Off. . |

(List continued on next page.)

OTHER PUBLICATIONS

J. Chem. Soc. (1971), D. J. Brown, B. T. England: "The Dimroth Rearrangement".

(List continued on next page.)

Primary Examiner—Robert Gerstl
Attorney, Agent, or Firm—Sprung Horn Kramer & Woods

[57] ABSTRACT

The present invention relates to the use of substituted 1,2,4-oxadiazole derivatives of the general formula I

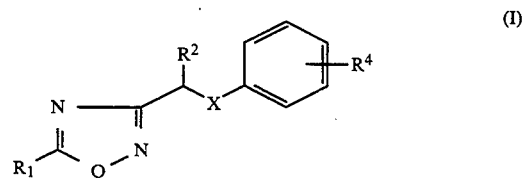

in which
R$^1$ represents hydrogen, alkyl which is optionally substituted by halogen, alkoxy, hydroxyl, amino, alkylamino, dialkylamino, cycloalkylamino as well as cycloalkyl, optionally substituted aryl or hetaryl,
R$^2$ represents hydrogen and alkyl,
X represents O, S, SO, SO$_2$ and N-R$^3$,
R$^3$ represents hydrogen, alkyl, alkylcarbonyl or halogenoalkylcarbonyl
R$^4$ represents identical or different radicals from the series comprising hydrogen, halogen, cyano, nitro, isothiocyanato, amino, aminoacyl, alkylamino, dialkylamino, trialkylammonium halide, sulphonylamino, hydroxyl, mercapto, alkyl, aralkyl, halogenoalkyl, alkoxy, aralkoxy, halogenoalkoxy, aryl, aryloxy, arylthio, arylsulphinyl, arylsulphonyl, alkylthio, halogenoalkylthio, alkylsulphinyl, halogenoalkylsulphinyl, alkylsulphonyl, halogenoalkylsulphonyl, alkoxycarbonyl, alkylcarbonyl, alkylcarbonyloxy, alkoxyalkyl, alkoxyalkoxy, hydroxyalkoxy, hetarylmethyleneoxy, for combating endoparasites in medicine and veterinary medicine, and new compounds of the formula (I) and their preparation.

4 Claims, No Drawings

FOREIGN PATENT DOCUMENTS

| | | |
|---|---|---|
| 1620574 | 4/1970 | Germany . |
| 57-175177 | 10/1982 | Japan . |
| 1198726 | 11/1967 | United Kingdom . |
| 2163427 | 2/1986 | United Kingdom . |
| 2205101 | 11/1988 | United Kingdom . |

OTHER PUBLICATIONS

A. R. Katritzky/C. W. Rees in "Comprehensive Heterocyclic Chemistry", Pergamon Press, Oxford/New York, 1984, vol. 3, pp. 93–98.

J. Heterocycl. Chem. 16 (1979) pp. 1469–1475.

Derwent abstract 93-073855/09 (1990).

Derwent abstract 92-062062/08 (1990).

Derwent abstract 92-185001/23 (1990).

Chemical abstract 98:198238y, "Ethyloxadiazole derivatives" (1983).

Chemical Abstracts, vol. 110, No. 19, 1989, Abstract No. 173224u, p. 776.

Chemical Abstracts, vol. 98, No. 23, 1983, Abstract No. 198238y, p. 657.

USE OF SUBSTITUTED 1,2,4-OXADIAZOLE DERIVATIVES FOR COMBATING ENDOPARASITES, NEW SUBSTITUTED 1,2,4-OXADIAZOLE DERIVATIVES, AND PROCESSES FOR THEIR PREPARATION

The present invention relates to the use of substituted 1,2,4-oxadiazole derivatives for combating endoparasites, new substituted 1,2,4-oxadiazole derivatives, and processes for their preparation.

Various substituted 1,2,4-oxadiazole derivatives have already been disclosed as compounds used for combating parasitic protozoa (cf. EP 7,529, EP 8,356), as pain killers (GB 1,198,726) or as herbicides (JP 57 175-177). However, nothing has been disclosed about a use of these compounds against endoparasites.

The present invention relates to:

1. The use of substituted 1,2,4-oxadiazole derivatives of the general formula I

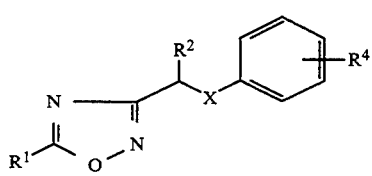

in which
R$^1$ represents hydrogen, alkyl which is optionally substituted by halogen, alkoxy, hydroxyl, amino, alkylamino, dialkylamino, cycloalkylamino as well as cycloalkyl, optionally substituted aryl or hetaryl,
R$^2$ represents hydrogen and alkyl,
X represents O, S, SO, SO$_2$ and N-R$^3$,
R$^3$ represents hydrogen, alkyl, alkylcarbonyl or halogenoalkylcarbonyl
R$^4$ represents identical or different radicals from the series comprising hydrogen, halogen, cyano, nitro, isothiocyanato, amino, aminoacyl, alkylamino, dialkylamino, trialkylammonium halide, sulphonylamino, hydroxyl, mercapto, alkyl, aralkyl, halogenoalkyl, alkoxy, aralkoxy, halogenoalkoxy, aryl, aryloxy, arylthio, arylsulphinyl, arylsulphonyl, alkylthio, halogenoalkylthio, alkylsulphinyl, halogenoalkylsulphinyl, alkylsulphonyl, halogenoalkylsulphonyl, alkoxycarbonyl, alkylcarbonyl, alkylcarbonyloxy, alkoxyalkyl, alkoxyalkoxy, hydroxyalkoxy, hetarylmethyleneoxy, for combating endoparasites in medicine and veterinary medicine.

Some of the compounds of the formula (I) are known and can be prepared analogously to known processes.

2. New substituted 1,2,4-oxadiazole derivatives of the general formula (I)

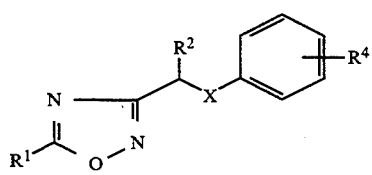

in which

R$^1$ represents hydrogen, C$_1$-C$_4$-alkyl which is optionally substituted by halogen, optionally substituted aryl or hetaryl, in particular furyl, thienyl as well as pyridyl,
R$^2$ represents hydrogen and C$_1$-C$_4$-alkyl,
X, in the event that R$^2$ represents C$_{1-4}$-alkyl, represents O, S, SO, SO$_2$ and N-R$^3$,
X, in the event that R$^2$ represents hydrogen, represents O, SO, SO$_2$ and N-R$^3$,
R$^3$ represents hydrogen, alkyl, alkylcarbonyl or halogenoalkylcarbonyl,
R$^4$ represents hydrogen, halogen, cyano, nitro, isothiocyanato, amino, aminoacyl, alkylamino, dialkylamino, trialkylammonium halide, sulphonylamino, hydroxyl, mercapto, alkyl, aralkyl, halogenoalkyl, alkoxy, aralkoxy, halogenoalkoxy, aryl, aryloxy, arylthio, arylsulphinyl, arylsulphonyl, alkylthio, halogenoalkylthio, alkylsulphinyl, halogenoalkylsulphinyl, alkylsulphonyl, halogenoalkylsulphonyl, alkoxycarbonyl, alkylcarbonyl, alkylcarbonyloxy, alkoxyalkyl, alkoxyalkoxy, hydroxyalkoxy, hetarylmethyleneoxy, 3. New substituted 1,2,4-oxadiazole derivatives of the general formula (I)

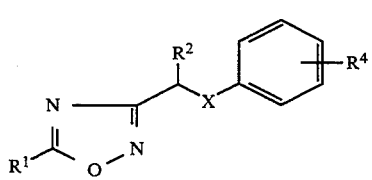

in which
R$^1$ represents hydrogen, C$_1$-C$_4$alkyl which is optionally substituted by halogen, optionally substituted aryl or hetaryl, in particular furyl, thienyl as well as pyridyl,
R$^2$ represents hydrogen,
X represents S,
R$^4$ represents 2-Cl; 3-Cl; 2,3-Cl$_2$; 2,4-Cl$_2$; 2,5-Cl$_2$, 2,6-Cl$_2$, 2,4,6-Cl$_2$; 2-F, 3-Cl; 2-Cl; 4-F; 2,3-F$_2$; 3-Br; 3,4-OCHF—CF$_2$—O; 2-OCF$_3$; 4-OCF$_3$; 3-CF$_3$; 4-Cl; 4-CF$_3$, 3,5-(CF$_3$)$_2$; 3,5-(CH$_3$)$_2$; 3,4-(OCH$_3$)$_2$; 2,5-(OCH$_3$)$_2$; 4-nC$_9$H$_{19}$; 4-N(C$_2$H$_5$)$_2$; 4-NH—CH$_3$; 4-NH—C$_2$H$_5$; 4-NH—CO—CH$_3$; 4-N$^+$(CH$_3$)$_3$Cl$^-$; 4-N$^+$(CH$_3$)$_3$I$^-$,
where R$^4$ in the event that R$^1$ has a meaning other than hydrogen, additionally represents 3,4-Cl$_2$; 2,4,5-Cl$_3$; 4-F; 2-Br; 3-CF$_3$; 2-CH$_3$; 3-CH$_3$; 4-CH$_3$; 2,4-(CH$_3$)$_2$; 2,6(CH$_3$)$_2$; 4-OH; 4-O—OC—CH$_3$; 2-OCH$_3$; 3-OCH$_3$; 4-OCH$_3$; 4-tC$_4$H$_9$; 4-NCS; 4-NH$_2$; 4-NH—CH$_3$; 4-N(CH$_3$)$_2$; 4-N(C$_2$H$_5$)$_2$.

4. Processes for the preparation of the new substituted 1,2,4-oxadiazole derivatives of the formula (I)

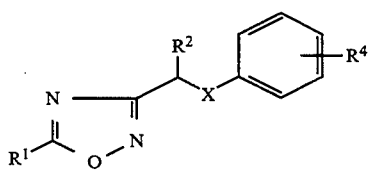

in which
X, R$^1$, R$^2$, R$^3$ and R$^4$ have the meaning given under items 2 and 3, characterised in that
a) compounds of the formula (II)

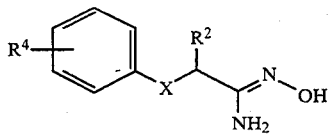
(II)

in which
X, $R^2$, $R^3$ and $R^4$ have the abovementioned meaning, are reacted with carboxylic acid derivatives the formulae (III), (IV) or (V)

$$R^1\text{-C(O-R)}_3 \quad \text{(III)}$$

$$(R^1\text{-CO})_2\text{O} \quad \text{(IV)}$$

$$R^1\text{-CO-Y} \quad \text{(V)}$$

in which
$R^1$ has the abovementioned meaning and R preferably represents methyl or ethyl, and Y represents a suitable leaving group, or
b) compounds of the formula (VI)

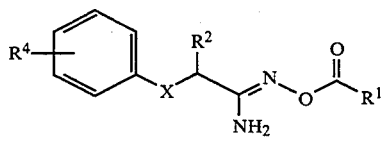
(VI)

in which
X, $R^1$, $R^2$, $R^3$ and $R^4$ have the abovementioned meaning,
are cyclised, if appropriate in the presence of a diluent and if appropriate in the presence of a reaction auxiliary, or
c) compounds of the formula (VII)

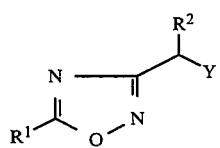
(VII)

in which
$R^1$ and $R^2$ have the abovementioned meaning, and
Y represents a suitable leaving group
are reacted with compounds of the formula (VIII)

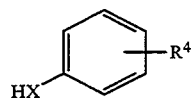
(VIII)

in which
X and $R^4$ have the abovementioned meaning,
in the presence of a diluent and if appropriate in the presence of a reaction auxiliary.

Formula (I) provides a general definition of the substituted 1,2,4-oxadiazole derivatives according to the invention.

Preferred compounds of the formula (I) are those in which $R^1$ represents hydrogen, $C_1$–$C_4$-alkyl which is optionally substituted by halogen, in particular fluorine, chlorine or bromine, $C_1$–$C_4$-alkoxy, in particular methoxy or ethoxy, hydroxyl, amino, $C_1$–$C_4$-alkylamino, in particular methylamino, $C_1$–$C_1$-dialkylamino, in particular dimethylamino or diethylamino, as well as cyclo-$C_3$–$C_7$-alkylamino, in particular cyclopropylamino, cyclopentylamino or cyclohexylamino, cyclo-$C_3$–$C_7$-alkyl, in particular cyclopropyl, cyclopentyl or cyclohexyl, optionally substituted phenyl or hetaryl, in particular furyl, thienyl as well as pyridyl, $R^2$ represents hydrogen and $C_1$–$C_4$-alkyl, in particular methyl, X represents O, S, SO, $SO_2$ and —N-$R^3$, $R^3$ represents hydrogen, $C_1$–$C_4$-alkyl, in particular methyl or ethyl, $C_1$–$C_4$-alkylcarbonyl, in particular acetyl or propionyl, halogeno-$C_1$–$C_4$-alkylcarbonyl, in particular trifluoroacetyl, $R^4$ represents identical or different radicals from the series comprising hydrogen, halogen, in particular fluorine, chlorine or bromine, cyano, nitro, isothiocyanato, amino, $C_1$–$C_4$-alkylamino, in particular methylamino or ethylamino, $C_1$–$C_4$-dialkylamino, in particular dimethylamino, $C_1$–$C_4$-trialkylammonium halide, in particular trimethylammonium bromide, trimethylammonium chloride or trimethylammonium iodide, sulphonylamino, hydroxyl, mercapto, $C_1$–$C_9$-alkyl, in particular methyl, ethyl, isopropyl, butyl, hexyl, octyl or nonyl, aralkyl, halogeno-$C_1$–$C_4$-alkyl, in particular trifluoromethyl, $C_1$–$C_4$-alkoxy, in particular methoxy, ethoxy, methylenedioxy or ethylenedioxy, each of which is optionally substituted by fluorine or chlorine, halogeno-$C_1$–$C_4$-alkoxy, in particular trifluoromethoxy, fluorochloroethoxy, aralkoxy, aryl, aryloxy, arylthio, arylsulphinyl, arylsulphonyl, $C_1$–$C_4$-alkylthio, in particular methylthio, $C_1$–$C_4$-halogenoalkylthio, in particular trifluoromethylthio, fluorochloromethylthio, $C_1$–$C_4$-alkylsulphinyl, in particular methylsulphinyl, $C_1$–$C_4$-halogenoalkylsulphinyl, in particular trifluoromethylsulphinyl, $C_1$–$C_4$-alkylsulphonyl, in particular methylsulphonyl, $C_1$–$C_4$-halogenoalkylsulphonyl, in particular trifluoromethylsulphonyl, alkoxycarbonyl, in particular methoxy- or ethoxycarbonyl, alkylcarbonyl, in particular acetyl or propionyl as well as oxadiazolylmethyleneoxy which is substituted by one of the radicals indicated for $R^1$.

Particularly preferred compounds of the formula (I)

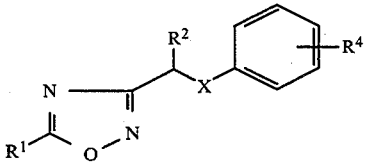
(I)

are those in which
$R^1$ represents hydrogen, $C_1$–$C_4$-alkyl, in particular methyl, ethyl, isopropyl or sec. butyl, $C_1$–$C_4$-halogenoalkyl, in particular trichloromethyl or trifluoromethyl, $R^2$ represents hydrogen, $C_1$–$C_4$-alkyl, in particular methyl, X represents O, S, SO, SO$_2$ and —N-R$^3$, R$^3$ represents hydrogen, C$_1$-C$_4$-alkylcarbonyl, in particular acetyl or propionyl, halogeno-C$_1$-C$_4$-alkylcarbonyl, in particular trifluoroacetyl, R$^4$ represents identical or different radicals from the series comprising hydrogen, halogen, in particular fluorine, chlorine or bromine, nitro, isothiocyanato, amino, C$_1$-C$_4$-alkylamino, in particular methylamino or ethylamino, C$_1$-C$_4$-dialkylamino, in particular dimethylamino, C$_1$-C$_4$-trialkylammonium halide, in particular trimethylammonium bromide, trimethylammonium chloride or trimethylammonium iodide, hydroxyl, mercapto, C$_1$-C$_9$-alkyl, in particular methyl, ethyl, isopropyl, butyl, hexyl, octyl or nonyl, halogeno-C$_1$-C$_4$-alkyl, in particular trifluoromethyl, C$_1$-C$_4$-alkoxy, in particular methoxy, ethoxy, methylenedioxy or ethylenedioxy, each of which is optionally substituted by fluorine or chlorine, halogeno-C$_1$-C$_4$-alkoxy, in particular trifluoromethoxy, fluorochloroethoxy, C$_1$-C$_4$-alkylthio, in particular methylthio, C$_1$-C$_4$-halogenoalkylthio, in particular trifluoromethylthio, fluorochloromethylthio, C$_1$-C$_4$-alkylsulphinyl, in particular methylsulphinyl, C$_1$-C$_4$-halogenoalkylsulphinyl, in particular trifluoromethylsulphinyl, C$_1$-C$_4$-alkylsulphonyl, in particular methylsulphonyl, C$_1$-C$_4$-halogenoalkylsulphonyl, in particular trifluoromethylsulphonyl, as well as 3-(1,2,4-oxadiazolyl)methyleneoxy, which is substituted in the 5-position by one of the radicals given under R$^1$.

Very particularly preferred compounds of the formula (I) are those in which

R$^1$ represents hydrogen, C$_1$-C$_1$-alkyl, in particular methyl, C$_1$-C$_4$-halogenoalkyl, in particular trichloromethyl or trifluoromethyl, R$^2$ represents hydrogen, C$_1$-C$_1$-alkyl, in particular methyl, X represents O, S, SO, SO$_2$, and —N-R$^3$, R$^3$ represents hydrogen, C$_1$-C$_4$-alkylcarbonyl, in particular acetyl, halogeno-C$_1$-C$_4$-alkylcarbonyl, in particular trifluoroacetyl, R$^4$ represents identical or different radicals from the series comprising hydrogen, halogen, in particular fluorine, chlorine or bromine, nitro, amino, C$_1$-C$_4$-dialkylamino, in particular dimethylamino, C$_1$-C$_4$-trialkylammonium halide, in particular trimethylammonium bromide, trimethylammonium chloride or trimethyl ammonium iodide, hydroxyl, C$_1$-C$_4$-alkyl, in particular methyl, ethyl or isopropyl, halogeno-C$_1$-C$_4$-alkyl, in particular trifluoromethyl, C$_1$-C$_4$-alkoxy, in particular methoxy, methylenedioxy or ethylenedioxy, each of which is optionally substituted by fluorine or chlorine, halogeno-C$_1$-C$_4$-alkoxy, in particular trifluoromethoxy, fluorochloroethoxy, C$_1$-C$_4$-alkylthio, in particular methylthio, C$_1$-C$_4$-halogenoalkylthio, in particular trifluoromethylthio, fluorochloromethylthio, as well as 3-(5-trifluoromethyl-1,2,4-oxadiazolyl)-methyleneoxy.

The compounds of the formula (I) which are to be used according to the invention, in which R$^2$ preferably represents methyl, contain at least one asymmetrically substituted carbon atom and can therefore exist in various enantiomeric forms. The invention relates to the individual isomers which are possible as well as to mixtures of these isomers.

The following compounds of the formula (I) in which the radicals R$^1$, R$^2$, R$^3$ and R$^4$ have the following meaning may be mentioned specifically:

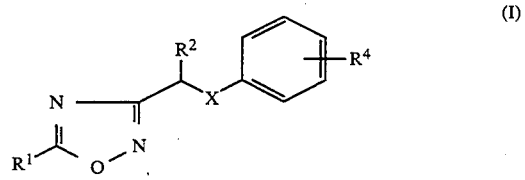

3-(2-fluoro-4-chloro-phenoxymethyl)-1,2,4-oxadiazole,
3-(2-fluoro-3-chloro-phenoxymethyl)-5-methyl-1,2,4-oxadiazole,
3-[2-(2-fluoro-3-chloro-phenoxy)ethyl]-1,2,4-oxadiazole,
3-(2,6-dichloro-phenoxymethyl)-1,2,4-oxadiazole,
3-(2,6-dichloro-phenoxymethyl)-5-methyl-1,2,4-oxadiazole,
3-[2-(2,6-dichloro-phenoxy)-ethyl]-1,2,4-oxadiazole,
3-[2-(2-fluoro-3-chloro-phenylthio)-ethyl]-1,2,4-oxadiazole,
3-[2-(2-fluoro-3-chloro-phenylthio)-ethyl]-5-methyl-1,2,4-oxadiazole,
3-(3,4-dimethoxy-phenylthiomethyl)-1,2,4-oxadiazole,
3-(2 5-dimethoxy-phenylthiomethyl)-5-methyl-1,2,4-oxadiazole,
3-(2,6-dichloro-phenylsulphoxylmethyl-5-methyl-1,2,4-oxadiazole,
3-(2,6-dimethyl-phenylsulphoxylmethyl)-5-methyl-1,2,4-oxadiazole,
3-(2,6-dichloro-phenylaminomethyl)-1,2,4-oxadiazole,
3-(2,6-dichloro-phenylaminomethyl)-5-methyl-1,2,4-oxadiazole,
3-(2-fluoro-3-chloro-phenylaminomethyl)-1,2,4-oxadiazole,
3-(2-fluoro-3-chloro-phenylaminomethyl)-5-methyl-1,2,4-oxadiazole,
3-(4-methoxy-phenylaminomethyl)-5-methyl-1,2,4-oxadiazole,
3-(N-trifluoroacetyl-2,6-dichloro-phenylaminomethyl)-5-methyl-1,2,4-oxadiazole,
3-(N-acetyl-2,6-dichloro-phenylaminomethyl)-5-methyl-1,2,4-oxadiazole.

Preferred and particularly preferred compounds from amongst the new compounds of the formula (I) are those in which the abovementioned preferred definitions apply to the substituents.

Some of the compounds of the formula (I) are known; they can be prepared by processes a) to c) which have been mentioned above under item 3 (cf., for example, EP 8,356, EP 7,529; cf. also Reviews: F. Eloy Fortschr. chem. Forsch. 4 (1965) P. 807; L. C. Behr in "The Chemistry of Heterocyclic Compounds", Vol. 17, (1962) p. 245; B. C. Leallyn in "Advances in Heterocyclic Chemistry", Vol. 20, Edited by A. R. Katritzky, A. J. Boulton, Academic Press, New York, San Francisco, London, 1976, p. 65).

If, in process 3a) for the preparation of the new substituted 1,2,4-oxadiazole derivatives, 3-chloro-2-methyl-phenoxy-acetamide oxime is employed as compounds of the formula (II) and triethyl orthoformate as compound of the formula (III), the process can be represented by the following equation.

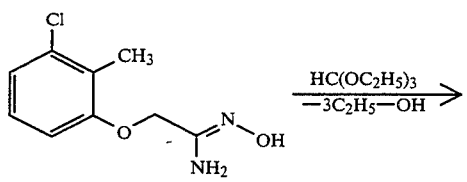
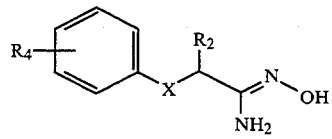
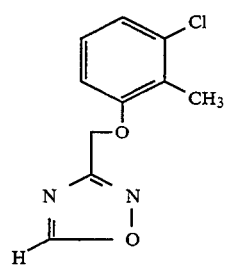

Formula (II) provides a general definition of the amide oximes required as starting substances for carrying out process 3a) according to the invention. In this formula, X, R², R³ and R⁴ preferably represent those radicals which have already been mentioned in connection with the description of the substances of the formula (I) according to the invention as being preferred for these substituents.

Some of the compounds of the formula (II), which are used as starting materials, are known (cf., for example, Cervena et al., Collect. Czech. Chem. Commun. 46 (1981) 5, pp. 1188–1198, EP 8,356, EP 7,529) or can be obtained by the processes described in these publications.

Formula (III) provides a general definition of the carboxylic acid orthoesters furthermore to be used as starting substances for carrying out process 3a) according to the invention. Formulae (IV) and (V) provide general definitions of the carboxylic acid derivatives which are additionally suitable for carrying out process 3a) according to the invention. In formulae (III) to (V), R¹ has the meaning which have already been mentioned in connection with the description of the substances of the formula (I) according to the invention as being preferred for this substituent. In formula (IV), Y has the meaning of a suitable leaving group, such as, for example, halogen or alkoxy. The carboxylic acid orthoesters of the formula (III) and the carboxylic acid derivatives of the formula (IV) and (V) are generally known compounds of organic chemistry.

The following compounds of the formula (II) may be mentioned individually:

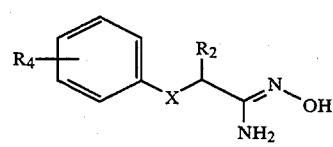

(II)

| X | R² | R⁴ | S | R² | R⁴ |
|---|---|---|---|---|---|
| O | H | 4-OCH₃ | S | CH₃ | 2-F, 3-Cl |
| O | CH₃ | 4-OCH₃ | S | CH₃ | 2,6-Cl₂ |
| O | H | 2-F, 3-Cl | S | CH₃ | 2,6-(CH₃)₂ |
| O | CH₃ | 2-F, 3-Cl | S | CH₃ | 2-OCH₂ |
| O | H | 2,6-Cl₂ | S | CH₃ | 3-OCH₃ |
| O | CH₃ | 2,6-Cl₂ | NH | CH₃ | 2-F, 3-Cl |
| O | H | 2,6-(CH₃)₂ | NH | H | 2,6-Cl₂ |
| O | H | 2-CH₃, 3-Cl | NH | H | 2,6-(CH₃)₂ |

-continued (II)

[structure of formula (II)]

| X | R² | R⁴ | S | R² | R⁴ |
|---|---|---|---|---|---|
| O | H | 3-OCH₃ | NH | CH₃ | 2-F, 3-Cl |

The compounds of the formula (II) and (III) are preferably reacted in the presence of an acidic catalyst. Catalysts which are suitable for this purpose are virtually all mineral acids or Lewis acids. The mineral acids preferably include hydrohalic acids such as hydrofluoric acid, hydrochloric acid, hydrobromic acid or hydriodic acid as well as sulphuric acid, phosphoric acid, phosphorous acid, nitric acid, and the Lewis acids preferably include aluminium(III) chloride, boron trifluoride or its etherate, titanium(IV) chloride and tin(IV) chloride.

The following Lewis acids are particularly preferably employed:

Boron trifluoride or its etherate, aluminium(III) chloride.

Process 3a) is carried out by combining compounds of the formula (II) with an excess of compounds of the formula (III) and heating the mixture in the presence of an acidic catalyst. In this case, the compound (II) simultaneously acts as diluent. The reaction time is approximately 1 to 4 hours. The reaction is carried out at temperatures between +20° C. and +200° C., preferably between +100° C. and +155° C. The process is preferably carried out under the pressure which is established under the reaction conditions when the mixture is heated to the reaction temperature required.

When the reaction is complete, the reaction mixture is cooled and concentrated in vacuo, the residue which remains is taken up in an organic solvent, and the mixture is worked up in a known manner. The products which are obtained can be purified in the customary manner by recrystallisation, distillation in vacuo or column chromatography (cf. also the preparation examples).

Alternatively, this reaction can also be carried out using a Meerwein reagent (for example a dialkyl acetal of dimethylformamide) or using the Vilsmeier-Haack reagent (POCl₃, N,N-dimethylformamide).

If, in process 3b), O-benzoyl-(4-chloro-phenoxy)acetamide oxime is employed as compounds of the formula (VI), the process can be described by the following equation:

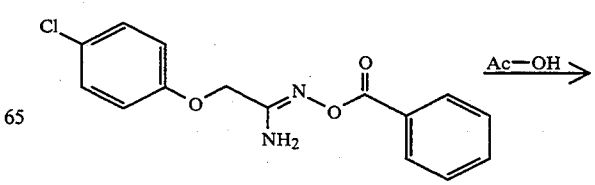

-continued

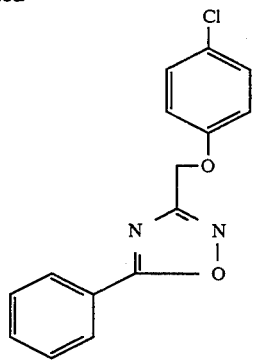

Compounds of the formula (VI) which are preferably employed in process 3b) are those in which X and the radicals $R^1$, $R^2$, $R^3$ and $R^4$ have the meanings which have been mentioned as preferred and particularly preferred in the case of the compounds of the formula (I).

The compounds of the formula (VI) can be formed, in process 3a), in situ from compounds of the formula (II) and suitable carboxylic acid derivatives of the formula (IV) and (V), but they can also be employed in isolated form, as is the case here in process 3b).

The compounds of the formula (VI) are preferably cyclised using diluents, if appropriate in the presence of a reaction auxiliary.

Diluents which are suitable for carrying out process 3b) according to the invention are all inert organic solvents.

Examples which must be mentioned are: halogenohydrocarbons, in particular chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, dichlorobenzene, chlorotoluene, trichlorobenzene; alcohols such as methanol, ethanol, isopropanol, butanol; ethers such as ethyl propyl ether, methyl tert.-butyl ether, n-butyl ether, di-n-butyl ether, di-isobutyl ether, di-iso-amyl ether, di-isopropyl ether, anisole, phenetole, cyclohexyl methyl ether, diethyl ether, ethylene glycol dimethyl ether, tetrahydrofuran, dioxane, dichlorodiethyl ether, nitrohydrocarbons such as nitromethane, nitroethane, nitrobenzene, chloronitrobenzene, o-nitrotoluene; nitriles such as acetonitrile, butyronitrile, isobutyronitrile, benzonitrile, m-chlorobenzonitrile; aliphatic, cycloaliphatic or aromatic hydrocarbons such as heptane, hexane, nonane, cymene, benzine fractions within a boiling point range from 70° C. to 190° C., cyclohexane, methylcyclohexane, petroleum ether, ligroin, octane, benzene, toluene, xylene; esters such as ethyl acetate, isobutyl acetate; amides, for example formamide, N-methyl ethyl ketone, carboxylic acids such as acetic acid, propionic acid, butyric acid. Mixtures of the abovementioned solvents and diluents are also suitable.

Preferred substances are carboxylic acids such as acetic acid, or aromatic hydrocarbons such as toluene and xylene.

Reaction auxiliaries which can be used are all suitable dehydration reagents such as, for example, dicyclohexylcarbodiimide [DCC] (cf., for example F. Eloy Fortschr. chem. Forsch. 4 (1965) p. 807).

Process 3b) is carried out by heating compounds of the formula (VI) in a suitable diluent, if appropriate in the presence of a suitable reaction auxiliary. The reaction time is approximately 1 to 10 hours. The reaction is carried out at temperatures between +20° C. and +200° C., preferably between +70° C. and +170° C. The process is preferably carried out under the pressure which is established under the reaction conditions when the mixture is heated to the reaction temperature required.

When the reaction is complete, the reaction mixture is cooled, the entire batch is concentrated, the residue is taken up in an organic solvent, and the mixture is worked up in a manner known per se. The products obtained can be purified in the customary manner by recrystallisation, distillation in vacuo or column chromatography (cf. also the preparation examples).

If, in process 3c) for the preparation of the new 1,2,4-oxadiazole derivatives, 3-chloromethyl-5-methyl-1,2,4-oxadiazole is employed as compounds of the formula (VII) and 2,3-dichloro-thiophenol as compounds of the formula (VIII), the process can be represented by the following equation:

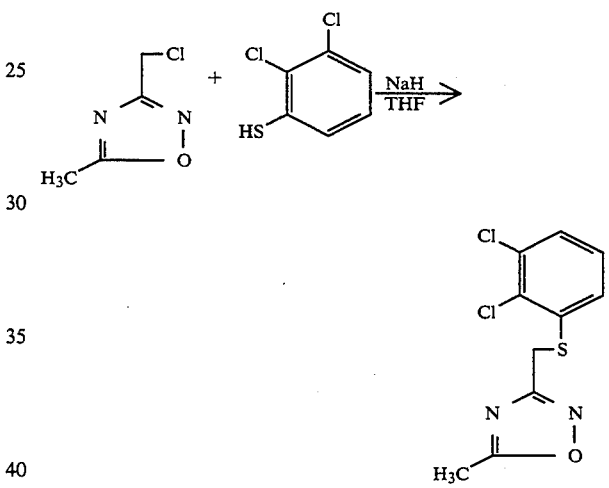

Formula (VII) provides a general definition of the 3,5-disubstituted 1,2,4-oxadiazoles required as starting substances for carrying out process 3c) according to the invention. In this formula, Y, $R^1$ and $R^2$ preferably represent those radicals which have already been mentioned in connection with the description of the substances of the formula (I) according to the invention as being preferred for these substituents.

Some of the compounds of the formula (VII), which are used as starting materials, are known (cf., for example, DE-OS (German Published Specification) 2,406,786, GB 2,205,101; G. Palazzo J. Heterocyclic Chem. 16 (1979) p. 1469) or can be obtained by the processes described in these publications.

The following compounds of the formula (VII) may be mentioned individually as starting component in which Y as well as the radicals $R^1$ and $R^2$ have the following meaning.

3-Chloromethyl-1,2,4-oxadiazole,
3-(2-chloroethyl)-1,2,4-oxadiazole,
3-chloromethyl-5-methyl-1,2,4-oxadiazole,
3-(2-chloroethyl)-5-methyl-1,2,4-oxadiazole,
3-chloromethyl-5-trifluoromethyl-1,2,4-oxadiazole,
3-(2-chloroethyl)-5-trifluoromethyl-1,2,4-oxadiazole,
3-chloromethyl-5-trichloromethyl-1,2,4-oxadiazole,
3-(2-chloroethyl )-5-trichloromethyl-1,2,4-oxadiazole, 3-chloromethyl-5-ethyl-1,2,4-oxadiazole,
3-(2-chloroethyl)-5-ethyl-1,2,4-oxadiazole,
3-chloromethyl-5-(2-chloro-6-fluoro-phenyl)-1,2,4-oxadiazole.

The compounds of the formula (VII) are preferably reacted using diluents, in the presence of a basic reaction auxiliary.

Basic reaction auxiliaries which can be employed are all suitable acid-binding agents such as amines, in particular tertiary amines as well as alkali metal and alkaline earth metal compounds.

Examples which may be mentioned are the hydrides, hydroxides, oxides and carbonates of lithium, sodium, potassium, magnesium, calcium and barium, furthermore other basic compounds such as trimethylamine, tribenzylamine, triisopropylamine, tributylamine, tribenzylamine, tricyclohexylamine, triamylamine, trihexylamine, N,N-dimethylaniline, N,N-dimethyl-toluidine, N,N-dimethyl-p-amino-pyridine, N-methyl-pyrrolidine, N-methylpiperidine, N-methyl-imidazole, N-methyl-pyrrole, N-methyl-morpholine, N-methyl-hexamethyleneimine, pyridine; quinoline, α-picoline, β-picoline, isoquinoline, pyrimidine, acridine, N,N,N',N'-tetra-methylenediamine, N,N,N'N'-tetra-ethylenediamine, quinoxaline, N-propyl-diisopropylamine, N,N'-dimethylcyclohexylamine, 2,6-lutidine, 2,4-lutidine, triethylenediamine, diazabicyclooctane (DABCO), diazabicyclononene (DBN) or diazabicycloundecene (DBU).

Tertiary amines such as, for example, triethylamine, N-methyl-morpholine, or heteroaromatic substances, or hydrides or hydroxides of potassium or of sodium, are preferably used.

Process 3c) is carried out by combining compounds of the formula (VII) with a small excess of compounds of the formula (VIII) and heating the mixture in the presence of a basic reaction auxiliary. The reaction time is approximately 5 to 30 hours. The reaction is carried out at temperatures between +20° C. and +200° C., preferably between +70° C. and +170° C. The process is preferably carried out under the pressure which is established under the reaction conditions when the mixture is heated to the reaction temperature required.

When the reaction is complete, the reaction mixture is cooled, the entire batch is filtered and concentrated in vacuo, and the crude product which remains is worked up in a manner known per se. The products obtained can be purified in the customary manner by recrystallisation, distillation in vacuo or, preferably, by column chromatography (cf. also the preparation examples).

In the compounds of the general formula (I) which have an arylthiomethyl radical and which have been synthesised by processes 3a) to 3c), the sulphur-containing group can be oxidised. The oxidation can be carried out by customary processes using suitable oxidants such as peroxides (for example $H_2O_2$), permanganate, perbenzoic acid, or using a mixture of potassium peroxomonosulphate, $2KHSO_5$, $KHSO_4$, and a solvent or solvent mixture (for example water, acetic acid, methanol) (cf. A. R. Katritzky, C. W. Rees in Comprehensive Heterocyclic Chemistry, Pergamon Press, Oxford, N.Y., 1984, Vol. 3, p. 96; D. J. Brown et al. Chem. Soc. (C), 1971, p. 256).

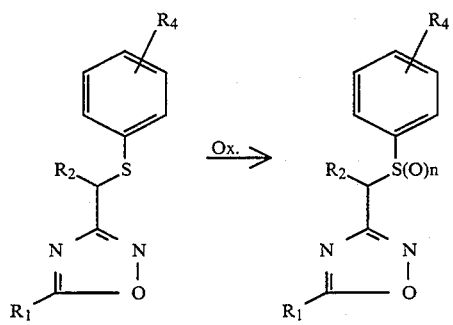

The oxidation can also be initiated or accelerated by means of catalysts.

While having low toxicity to warm-blooded species, the active compounds are suitable for combating pathogenic endoparasites which occur in humans and in animal keeping and livestock breeding, in productive livestock, breeding animals, zoo animals, laboratory animals, experimental animals and pets. In this context, they are active against all or individual stages of development of the pests and against resistant and normally sensitive species. By combating the pathogenic endoparasites, it is intended to reduce disease, deaths and decreasing performance (for example in the production of meat, milk, wool, hides, eggs, honey, etc.), so that more economical and simpler animal keeping is possible by using the active compounds. The pathogenic endoparasites include cestodes, trematodes and nematodes, in particular:

From the order of the Pseudophyllidea, for example: *Diphyllobothrium spp., Spirometra spp., Schistocephalus spp., Ligula spp., Bothridium spp., Diphlogonoporus spp.*

From the order of the Cyclophyllidea, for example: *Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.*

From the subclass of the Monogenea, for example: *Gyrodactylus spp., Dactylogyrus spp., Polystoma spp.*

From the subclass of the Digenea, for example: *Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.*

From the order of the Enoplida, for example: *Trichuris spp., Capillaria spp., Trichomosoides spp., Trichinella spp.*

From the order of the Rhabditia, for example: *Micronema spp., Strongyloides spp.*

From the order of the Strongylida, for example: *Stronylus spp., Triodontophorus spp., Oesophagodontus*

*spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.*

From the order of the Oxyurida, for example: *Oxyuris spp., Enterobius spp., Passalurus spp., Syphacia spp., Aspiculuris spp., Heterakis spp.*

From the order of the Ascaridia, for example: *Ascaris spp., Toxascaris spp., Toxocara spp., Parascaris spp., Anisakis spp., Ascaridia spp.*

From the order of the Spirurida, for example: *Gnathostoma spp., Physaloptera spp., Thelazia spp., Gongylonema spp., Habronema spp., Parabronema spp., Draschia spp., Dracunculus spp.*

From the order of the Filariida, for example: *Stephanofilaria spp., Parafilaria spp., Setaria spp., Loa spp., Dirofilaria spp., Litomosoides spp., Brugia spp., Wuchereria spp., Onchocerca spp.*

From the order of the Gigantorhynchida, for example: *Filicollis spp., Moniliformis spp., Macracanthorhynchus spp., Prosthenorchis spp.*

The productive livestock and breeding animals include mammals such as, for example, cattle, horses, sheep, pigs, goats, camels, water buffalos, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carp, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically.

The active compounds are administered, directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, suppositories, tablets, capsules, pastes, drinks, granules, drenches, boli, medicated feed or drinking water. Dermal administration is effected, for example, in the form of dipping, spraying, bathing, washing, pouring-on and spotting-on and dusting. Parenteral administration is effected, for example, in the form of injection (intramuscularly, subcutaneously, intravenously, intraperitoneally) or by implants.

Suitable preparations are:

Solutions such as solutions for injections, oral solutions, concentrates for oral administration after dilution, solutions for use on the skin or in body cavities, pour-on and spot-on formulations, gels;

Emulsions and suspension for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Solutions for injection are administered intravenously, intramuscularly and subcutaneously.

Solutions for injection are prepared by dissolving the active compound in a suitable solvent and, if appropriate, adding additives such as solubilisers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl acohol, glycerol, hydrocarbons, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilisers: solvents which enhance dissolution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the solutions for injection, it being possible to dispense with working under sterile conditions.

Solutions for use on the skin are applied dropwise, brushed on, rubbed in, splashed on or sprayed on or applied by dipping, bathing or washing. These solutions are prepared as described above in the case of solutions for injection.

It may be advantageous to add thickeners during the preparation. Thickeners are: inorganic thickeners such as bentonite, colloidal silica, aluminium monostearate, organic thickeners such as cellulose derivatives, polyvinyl alcohols and their copolymers, acrylates and metacrylates.

Gels are applied to, or brushed on, the skin, or introduced into body cavities. Gels are prepared by treating solutions which have been prepared as described in the case of the solutions for injection with such an amount of thickener that a clear substance of cream-like consistency is formed. Thickeners employed are the thickeners indicated further above.

Pour-on and spot-on formulations are poured onto, or splashed onto, limited areas of the skin, the active compound either penetrating the skin and acting systemically or being spread over the surface of the body.

Pour-on and spot-on formulations are prepared by dissolving, suspending or emulsifying the active compound in suitable solvents or solvent mixtures which are tolerated by the skin. If appropriate, other adjuvants such as colourants, resorption accelerators, antioxidants, light stabilisers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butylacetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2-dimethyl-4-oxy-methylene-1,3-dioxolane.

Colourants are all colourants which are released for use on animals and which can be dissolved or suspended.

Examples of resorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilisers are substances from the class of the benzophenones or novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenising this phase with the solvent of the other phase, with the aid of suitable emulsifiers and, if appropriate, other adjuvants such as colourants, resorption accelerators, preservatives, antioxidants, light stabilisers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: nonionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-$\beta$-iminodipropionate or lecithin;

anionic surfactants such as sodium lauryl sulphate, fatty alcohol ether sulphates, the monoethanol amine salt of mono/dialkyl polyglycol ether orthophosphoric esters;

cationic surfactants such as cetyltrimethylammonium chloride.

The following may be mentioned as other adjuvants: viscosity-increasing substances and substances which stabilise the emulsion, such as carboxymethylcellulose, methylcellulose and other cellulose and starch derivatives; polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of injection. They are prepared by suspending the active compound in an excipient liquid, if appropriate with the addition of further adjuvants such as wetting agents; colourants, resorption accelerators, preservatives, antioxidants and light stabilisers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, animal meals, cereal meals and coarse cereal meals and starches.

Adjuvants are preservatives, antioxidants and colourants which have already been indicated further above.

Other suitable adjuvants are the lubricants and gliding agents such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which are active against pathogenic endoparasites. Examples of such active compounds are L-2,3,5,6-tetrahydro-6-phenylimidazothiazole, benzimidazole carbamates, praziquantel, pyrantel, febantel.

Ready-to-use preparations contain the active compound in concentrations of from 10 ppm–20 percent by weight, preferably of from 0.1–10 percent by weight.

Preparations which are diluted prior to administration contain the active compound in concentrations of from 0.5–90 percent by weight, preferably of from 5 to 50 percent by weight.

In general, it has proved advantageous to administer amounts of approximately 1 to approximately 100 mg of active compound per kg of body weight per day, to achieve effective results.

EXAMPLE A

In-vivo Nematode Test

*Trichostrongylus colubriformis*/sheep

Sheep which have been infected experimentally with *Trichostrongylus colubriformis* were treated after the prepatent period of the parasite had elapsed. The active compounds were administered orally as pure active compound in gelatine capsules.

The degree of activity is determined by quantitatively counting the worm eggs excreted with the faeces before and after the treatment.

If the excretion of eggs after the treatment has stopped completely, this means that the worms have been aborted or are damaged to such an extent that they no longer produce eggs (dosis effectiva).

Active compounds which have been tested and effective dosage rates (dosis effectiva) can be seen from the table which follows.

| Active Compound Example No. | Dosis effectiva in mg/kg |
| --- | --- |
| 14 | 10 |
| 18 | 10 |
| 19 | 10 |
| 21 | 10 |
| 28 | 10 |
| 33 | 10 |
| 35 | 10 |
| 36 | 10 |
| 38 | 10 |
| 45 | 10 |
| 49 | 10 |
| 52 | 10 |

EXAMPLE B

In-vivo Nematode Test

*Haemonchus contortus*/sheep

Sheep which have been infected experimentally with *Haemonchus contortus* were treated after the prepatent period of the parasite had elapsed. The active compounds were administered orally as pure active compound in gelatine capsules.

The degree of activity is determined by quantitatively counting the worm eggs excreted with the faeces before and after the treatment.

If the excretion of eggs after the treatment has stopped completely, this means that the worms have been aborted or are damaged to such an extent that they no longer produce eggs (dosis effectiva).

Active compounds which have been tested and effective dosage rates (dosis effectiva) can be seen from the table which follows.

| Active Compound Example No. | Dosis effectiva in mg/kg |
| --- | --- |
| 1 | 10 |
| 13 | 10 |
| 15 | 10 |
| 16 | 10 |
| 17 | 10 |
| 45 | 10 |

PREPARATION EXAMPLE

Example 1

3-(3-Chloro-2-methyl-phenoxymethyl)-1,2,4-oxadiazole

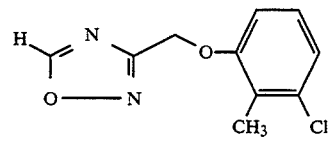

7.0 g (32.6 mmol) of 3-chloro-2-methyl-phenoxyacetamide oxime are introduced into 70 ml of triethyl orthoformate, and 5 drops of boron trifluoride etherate are added at room temperature. The mixture is subsequently stirred at reflux temperature until the reaction is complete (approximately 1 hour) and the entire batch is concentrated in vacuo. The residue is taken up in 100 ml of methylene chloride and washed in succession with 100 ml of 2N hydrochloric acid, saturated sodium carbonate solution and water. The organic phase is dried over sodium sulphate and the solvent is subsequently distilled off. The oily residue which remains is distilled using a bulb tube. 4.2 g (57.4% of theory) of 3-(3-chloro-2-methyl-phenoxymethyl)-1,2,4-oxadiazole are obtained.

B.p.$_{0.1\ mbar}$: 130° C.

$^1$H-NMR (DMSO-d$_6$, δ, ppm) 2.22 (s, 3H, arom. CH$_3$); 5.40 (s, 2H, —CH$_2$—O—); 6.86–7.30 (m, 3H, arom. H); 9.69 (s, 1H, hetarom. H).

Example 2

3-(3-Chloro-2-methyl-phenoxymethyl)-5-methyl-1,2,4-oxadiazole

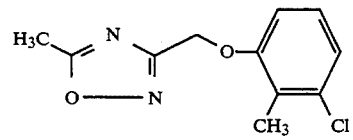

7.0 g (32.6 mmol) of 3-chloro-2-methyl-phenoxyacetamide oxime and 14.0 g (142.8 mmol) of sodium acetate are introduced into 80 ml of diglyme and the mixture is treated with 8.6 g (84.2 mmol) of acetic anhydride. The reaction mixture is stirred at reflux temperature until the reaction is complete (approximately 2 hours). The entire batch is subsequently concentrated, the product is treated with water, and the mixture is extracted using ethyl acetate. After the solvent has been distilled off, the crude product which remains is chromatographed over a silica gel column (silica gel 60 Merck, particle size: 0.040 to 0.063 mm) using methylene chloride as the eluent. 4.4 g (56.5% of theory) of 3-(3-chloro-2-methyl-phenoxymethyl)-5-methyl-1,2,4-oxadiazole are obtained.

M.p.: 69° C.

¹H-NMR (CDCl₃, δ, ppm) 2.30 (s, 3H, arom. CH₃); 2.61 (s, 3H, hetarom. CH₃); 5.14 (s, 2H, —CH₂—O—); 6.84–7.10 (m, 3H, arom. H);

Example 3

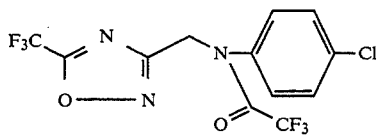

8.0 g (40.0 mmol) of 4-chloro-phenylamino-acetamide oxime are introduced into 90 ml of absolute tetrahydrofuran, the mixture is treated with 12.75 g (60.7 mmol) of trifluoroacetic anhydride and stirred at room temperature for 1.5 hours. The entire batch is subsequently concentrated in vacuo and the crude product which remains is chromatographed over a silica gel column (silica gel 60 Merck, particle size 0.040 to 0.063 mm) using chloroform: ethyl acetate (10:1) as the eluent. 5.4 g (36.1% of theory) of 3-(N-trifluoroacetyl-4-chlorophenylaminomethyl)-5-trifluoromethyl-1,2,4-oxadiazole and 3.0 g (27.0%) of 3-(4-chlorophenylaminomethyl)-5-trifluoro-1,2,4-oxadiazole are obtained.

3-(N-Trifluoroacetyl-4-chloro-phenylaminomethyl)-5-trifluoromethyl-1,2,4-oxadiazole ¹H-NMR (CDCl₃, δ, ppm): 5.08 (s, 2H, —CH₂—N—); 7.36; 7.43 (2d, 4H, arom. H; J=8.8 Hz)

Example 4

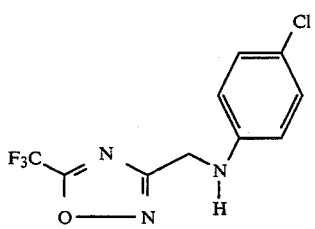

3-(4-Chloro-phenylaminomethyl)-5-trifluoromethyl-1,2,4-oxadiazole

¹H-NMR (CDCl₃, δ, ppm): 4.34 (br.s, 1H, —NH); 4.55 (s, 2H, —CH₂—O—); 6.63; 7.15 (2d, 4H, arom. H; J=8.8 Hz)

Example 5

3-[2,3,5-Trimethyl-4-(3-methyleneoxy-5-trifluoromethyl-1,2,4-oxadiazolyl)]-5-trifluoromethyl-1,2,4-oxadiazole

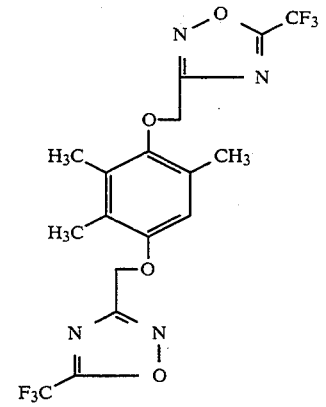

3.8 g (12.8 mmol) of bis-amide oxime are introduced into 40 ml of absolute tetrahydrofuran and treated with 8.5 g (40.4 mmol) of trifluoroacetic anhydride at room temperature. The entire batch is stirred for 1 hour at room temperature and then concentrated in vacuo, and the crude product which remains is chromatographed over a silica gel column (silica gel 60 Merck, particle size: 0.040 to 0.063 mm) using methylene chloride as the eluent. 2.6 g (44.2% of theory) of 3-[2,3,5-trimethyl-4-(3-methyleneoxy-5-trifluoromethyl-1,2,4-oxadiazolyl)]-5-trifluoromethyl-1,2,4-oxadiazole are obtained.

M.p.: 64° C.

¹H-NMR (CDCl₃), δ, ppm): 2.09; 2.23 (3s, 3H, —CH₃); 4.87; 5.15 (2s, 4H, —C

Example 6

3-(4-Chloro-phenoxymethyl)-5-phenyl-1,2,4-oxadiazole

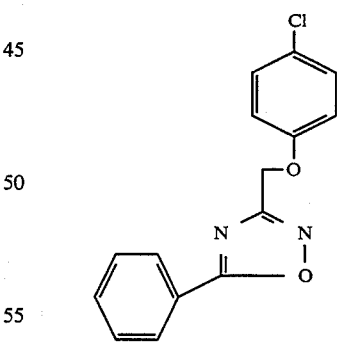

4.4 g (14.4 mmol) of O-benzoyl-(4-chloro-phenoxy)acetamide oxime are heated in 20 ml of glacial acetic acid until cyclisation is complete (after approximately 4 to 5 hours). The entire batch is subsequently concentrated in vacuo, the residue is taken up in ethyl acetate, the mixture is washed with water, and the organic phase is dried over sodium sulphate. The solvent is subsequently distilled off in vacuo, and the crude product which remains is chromatographed over a silica gel column (silica gel 60 Merck, particle size: 0.040 to 0.063 mm) using methylene chloride as the eluent. 1.3 g (31.5% of theory) of 3-(4-chloro-phenoxymethyl)-5-phenyl-1,2,4-oxadiazole are obtained.

M.p.: 96° to 102° C.

$^1$H-NMR (CDCl$_3$), δ, ppm): 5.22 (s, 2H, —CH$_2$—O—); 6.99; 7.26 (2d, 4H, arom. H; J=9.0 Hz); 7.50 to 8.17 (3m, 5H, arom. H)

Example 7

3-(2,3-Dichloro-phenylthiomethyl)-5-methyl-1,2,4-oxadiazole

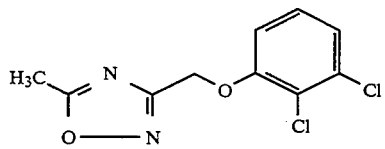

7.0 g (39.1 mmol) of 2,3-dichloro-thiophenol are introduced into 50 ml of absolute tetrahydrofuran, the mixture is treated with 1.2 g (0.039 mmol) of 80% sodium hydride dispersion in portions and stirred for 2 hours at reflux temperature. The mixture is subsequently treated with 4.5 g (33.9 mmol) of 3-chloromethyl-5-methyl-1,2,4-oxadiazole at room temperature and stirred until the reaction is complete (approximately 10 to 15 hours). The sodium chloride which has precipitated is subsequently separated off and the entire batch is concentrated in vacuo. The crude product which remains can be chromatographed over a silica gel column (silica gel 60-Merck, particle size: 0.040 to 0.063 mm) using toluene as the eluent. 3.8 g (36.5% of theory) of 3-(2,3-dichlorophenylthiomethyl)-5-methyl-1,2,4-oxadiazole are obtained.

M.p.: 66° to 68° C.

$^1$H-NMR (CDCl$_3$), δ, ppm): 2.57 (s, 3H, hetarom. H); 4.17 (s, 2H, —CH$_2$—S—); 7.13–7.36 (m, 3H, arom. H)

Example 8

3-(2,3-Dichloro-phenylsulphonylmethyl-5-methyl-1,2,4-oxadiazole

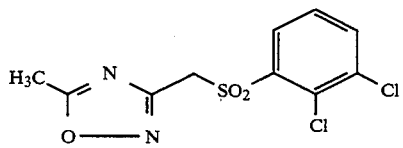

3.9 g (14.2 mmol) of 3-(2,3-dichloro-phenylthiomethyl)-5-methyl-1,2,4-oxadiazole are introduced into 50 ml of glacial acetic acid and the mixture is treated with 9.8 ml of 30% strength hydrogen peroxide. The mixture is stirred at reflux temperature until the reaction is complete (approximately 2 hours). The entire batch is then introduced into 200 ml of water, and the crude product which has precipitated is separated off and recrystallised from isopropanol. 1.7 g (38.9% of theory) of 3-(2,3-dichloro-phenylsulphonylmethyl)-5-methyl-1,2,4-oxadiazole are obtained.

M.p.: 105° to 107° C.

$^1$H-NMR (CDCl$_3$), δ, ppm): 2.55 (s, 3H, —CH$_3$); 4.86 (s, 2H, —CH$_2$—SO$_2$—); 7.35 to 7.95 (m, 3H, arom. H)

The compounds of the formula (I) which are listed in Table 1 below can be prepared analogously.

TABLE 1

Examples of the compounds of the formula (I)

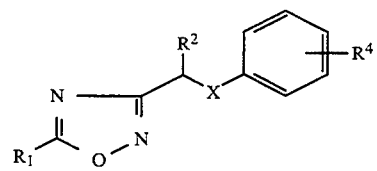

| Example No. | X | R$^1$ | R$^2$ | R$^4$ | Physical Data |
|---|---|---|---|---|---|
| 9 | O | H | H | H | m.p.: oil |
| 10 | O | CH$_3$ | H | H | m.p.: oil |
| 11 | O | CF$_3$ | H | H | m.p.: oil |
| 12 | O | H | H | 2-CH$_3$ | m.p.: oil |
| 13 | O | CH$_3$ | H | 2-CH$_3$ | m.p.: oil |
| 14 | O | H | H | 3-CH$_3$ | m.p.: oil |
| 15 | O | CH$_3$ | H | 3-CH$_3$ | m.p.: oil |
| 16 | O | H | H | 4-CH$_3$ | m.p.: oil |
| 17 | O | CH$_3$ | H | 4-CH$_3$ | m.p.: 34° C. |
| 18 | O | H | H | 4-OCH$_3$ | m.p.: oil |
| 19 | O | H | H | 2-Cl | m.p.: oil |
| 20 | O | CH$_3$ | H | 3-Cl | m.p.: oil |
| 21 | O | H | H | 4-Cl | m.p.: 56° C. |
| 22 | O | CH$_3$ | H | 4-Cl | m.p.: 82° C. |
| 23 | O | CF$_3$ | H | 4-Cl | m.p.: oil |
| 24 | O | H | H | 2,3-Cl$_2$ | |
| 25 | O | CH$_3$ | H | 2,4-Cl$_2$ | m.p.: 92° C. |
| 26 | O | CF$_3$ | H | 2,4-Cl$_2$ | m.p.: 33° C. |
| 27 | O | phenyl | H | 2,4-Cl$_2$ | m.p.: 81° C. |
| 28 | O | H | H | 4-CF$_3$ | m.p.: 48° C. |
| 29 | O | CF$_3$ | H | 2-CH$_3$,3-Cl | m.p.: oil |
| 30 | O | H | H | 2,3-(CH$_3$)$_2$ | m.p.: oil |
| 31 | O | CH$_3$ | H | 2,3-(CH$_3$)$_2$ | m.p.: oil |
| 32 | O | CF$_3$ | H | 2,3-(CH$_3$)$_2$ | m.p.: oil |
| 33 | O | H | H | 2,3,6-(CH$_3$)$_3$ | m.p.: oil |
| 34 | S | CH$_3$ | H | 2-CH$_3$ | m.p.: oil |
| 35 | S | CH$_3$ | H | 3-CH$_3$ | m.p.: oil |
| 36 | S | CH$_3$ | H | 4-CH$_3$ | m.p.: oil |
| 37 | S | CH$_3$ | H | 2-OCH$_3$ | m.p.: oil |
| 38 | S | CH$_3$ | H | 3-OCH$_3$ | m.p.: oil |
| 39 | S | CH$_3$ | H | 4-OCH$_3$ | m.p.: oil |
| 40 | S | CH$_3$ | H | 2-Cl | m.p.: oil |
| 41 | S | CH$_3$ | H | 3-Cl | m.p.: oil |
| 43 | S | CH$_3$ | H | 4-Cl | m.p.: 33–34° C. |
| 43 | S | CH$_3$ | H | 2,4-Cl$_2$ | m.p.: 47–49° C. |
| 44 | S | CH$_3$ | H | 3,4-Cl$_2$ | m.p.: 47–48° C. |
| 45 | S | CH$_3$ | H | 2,6-Cl$_2$ | m.p.: 84–85° C. |
| 46 | S | CH$_3$ | H | 4-F | m.p.: 33–34° C. |
| 47 | S | H | H | 2-F,3-Cl | m.p.: oil |
| 48 | S | CH$_3$ | H | 2-F,3-Cl | m.p.: oil |
| 49 | S | CH$_3$ | H | 4-CF$_3$ | m.p.: 27–28° C. |
| 50 | S | CH$_3$ | H | 3-CF$_3$,4-Cl | m.p.: oil |
| 51 | S | CH$_3$ | H | 2-Cl,6-CH$_3$ | m.p.: oil |
| 52 | S | CH$_3$ | H | 2,6-(CH$_3$)$_2$ | m.p.: 43–45° C. |
| 53 | S | CH$_3$ | H | 4-O-phenyl | m.p.: oil |
| 54 | S | CH$_3$ | H | 4-n-C$_9$H$_{19}$ | m.p.: oil |
| 55 | S | CH$_3$ | H | 4-NO$_2$ | m.p.: 78–80° C. |
| 56 | S | CH$_3$ | H | 3,4-O—CHF—CF$_2$—O— | m.p.: oil |
| 57 | SO$_2$ | CH$_3$ | H | 4-CH$_3$ | m.p.: 70–71° C. |
| 58 | SO$_2$ | CH$_3$ | H | 4-Cl | m.p.: 88–89° C. |
| 59 | SO$_2$ | CH$_3$ | H | 2,6-Cl$_2$ | m.p.: 147–148° C. |
| 60 | SO$_2$ | CH$_3$ | H | 3-Cl,4-CF$_3$ | m.p.: 88–89° C. |
| 61 | SO$_2$ | CH$_3$ | H | 2,4-Cl$_2$ | m.p.: 128° C. |
| 62 | SO$_2$ | CH$_3$ | H | 4-CF$_3$ | m.p.: |

TABLE 1-continued

Examples of the compounds of the formula (I)

(I)

| Example No. | X | R¹ | R² | R⁴ | Physical Data |
|---|---|---|---|---|---|
| 63 | S | CH₃ | H | 2,5-Cl₂ | 127–128° C. m.p.: |
| 64 | S | CH₃ | H | 2,4,6-Cl₃ | 36–38° C. m.p.: |
| 65 | S | CH₃ | H | 3,4-(OCH₃)₂ | 71–73° C. m.p.: |
| 66 | S | H | H | 2,6-Cl₂ | 32–34° C. m.p.: 36–38° C. |
| 67 | S | H | H | 2-OCH₃ | m.p.: oil |
| 68 | S | H | H | 3-OCH₃ | m.p.: oil |
| 69 | S | H | H | 4-OCH₃ | m.p.: oil |
| 70 | S | H | H | 4-CF₃ | m.p.: oil |
| 71 | S | H | H | 2,5-(OCH₃)₂ | m.p.: 45–47° C. |
| 72 | S | H | H | 2-Cl | m.p.: oil |
| 73 | S | H | H | 3-Cl | m.p.: oil |
| 74 | S | H | H | 2,5-Cl₂ | m.p.: 94–96° C. |
| 75 | S | H | H | 3,4-Cl₂ | m.p.: oil |
| 76 | S | H | H | 2-CH₃ | m.p.: oil |
| 77 | S | H | H | 3-CH₃ | m.p.: oil |
| 78 | S | H | H | 4-CH₃ | m.p.: oil |
| 79 | S | H | H | 2,6-(CH₃)₂ | m.p.: oil |
| 80 | S | H | H | 3-CF₃ | m.p.: oil |
| 81 | S | H | H | 4-F | m.p.: 54° C. |
| 82 | S | H | H | 4-O-phenyl | m.p.: 64–65° C. |
| 83 | O | 2,6-F₂-phenyl | H | 4-t-C₄H₉ | m.p.: 74–76° C. |
| 84 | NH | CH₃ | H | 3-Cl | m.p.: oil |
| 85 | NH | CH₃ | H | 2-OCH₃ | m.p.: oil |

Starting substances of the formula (II)

Example (II-1)

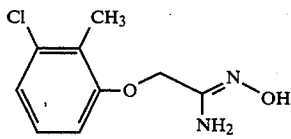

29.2 g (160.7 mmol) of 3-chloro-2-methyl-phenoxyacetonitrile are added to a solution of 13.5 g (194.2 mmol) of hydroxylamine hydrochloride, 7.7 g (194.2 mmol) of sodium hydroxide in 265 ml of ethanol and 68 ml of water. The mixture is heated at reflux temperature until the reaction is complete (approximately 48 to 60 hours) and the entire batch is subsequently stirred into 250 ml of water. The solid which precipitates in this process is separated off, washed with a small amount of water and dried. 31.1 g (90.2% of theory) of 3-chloro-2-methylphenoxyacetamide oxime are obtained.

¹H-NMR (DMSO-d₆, δ, ppm): 2.23 (s, 3H, arom. CH₃); 4.42 (s, 2H, —CH₂—O); 5.63 (s, 2H, —NH₂); 7.00–7.17 (m, 3H, arom. H); 9.31 (s, 1H, =N—OH);

¹³C NMR (DMSO-d₆, δ, ppm): 12.8 (—C̲H₃); 67.1 (—C̲H₂—O—); 110.9; 121.7 (arom. C̲); 124.6 (arom. C̲H₃); 133.9 (arom. C̲=N—); 157.3 (arom. C̲—O—)

Example (II-2)

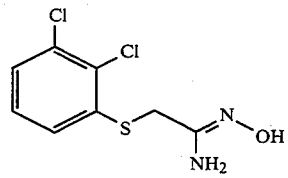

10.8 g (49.5 mmol) of 2,3-dichloro-phenylthioacetonitrile, 7.3 g (105.0 mmol) of hydroxylamine hydrochloride and 11.1 g (105.0 mmol) of sodium carbonate are stirred in 25 ml of ethanol and 50 ml of water at reflux temperature until the reaction is complete (approximately 24 hours). The entire batch is subsequently introduced into 200 ml of water, and the solid which precipitates in this process is filtered off with suction, washed with a small amount of water and dried. 12.2 g (98.1% of theory) of 2,3-dichloro-phenylthioacetamide oxime are obtained.

¹H-NMR (DMSO-d₆, δ, ppm): 5.62 (s, 2H, —NH₂); 7.30–7.56 (m, 3H, arom. H); 9.29 (br., 1H, =N—OH)

The compounds of the formula (II) which are listed in Table 2 below can be prepared analogously.

TABLE 2

Starting substances of the formula (II)

(II)

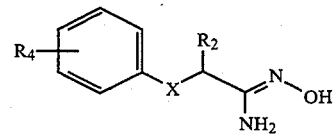

| Example No. | X | R² | R⁴ | Physical Data |
|---|---|---|---|---|
| II-3 | O | H | 2-CH₃ | 5.59; 9.29[b] |
| II-4 | O | H | 3-CH₃ | 4.94; 9.06[b] |
| II-5 | O | H | 4-CH₃ | 5.57; 9.26[b] |
| II-6 | O | H | 4-t-C₄H₉ | 4.91[a] |
| II-7 | O | H | 4-Cl | 5.62; 9.31[b] |
| II-8 | O | H | 2,4-Cl₂ | 5.64; 9.38[b] |
| II-9 | O | H | 3,4-Cl₂ | 5.66; 9.45[b] |
| II-10 | O | H | 3-Cl,4-CF₃ | 5.12; 9.16[b] |
| II-11 | NH | H | 4-Cl | 5.33; 9.01[b] |
| II-12 | S | H | 3,4-(OCH₃)₂ | 5.45; 9.11[b] |
| II-13 | S | H | 3,4-Cl₂ | 5.76; 9.22[b] |
| II-14 | S | H | 2-F,3-Cl | 5.59; 9.27[b] |
| II-15 | SO₂ | H | 4-CH₃ | 5.45; 9.38[b] |
| II-16 | SO₂ | H | 4-Cl | 5.50; 9.39[b] |

[a] ¹H-NMR (CDCl₃, δ, ppm)
[b] ¹H-NMR (DMSO-d₆, δ, ppm); in each case singlets (broad) for

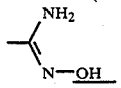

Example (VI-1)

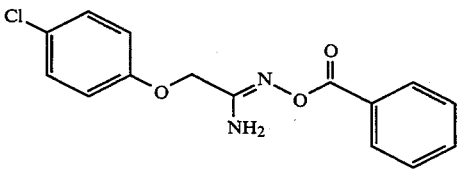

5.0 g (24.9 mmol) of 4-chloro-phenoxyacetamide oxime and 4.35 ml (27.7 mmol) of N,N-diisopropylethylamine ("Hünig's base") are introduced into 50 ml of chloroform, and 3.9 g (27.7 mmol) of benzoyl chloride are added dropwise at room temperature. The entire batch is stirred for 2 hours and then washed with water, dried over sodium sulphate and concentrated in vacuo. The crude product which remains is subsequently chromatographed over a silica gel column (silica gel 60 Merck, particle size: 0.040 to 0.063 mm) using methylene chloride:methanol (100:1) as eluent. 3.9 g (51.4% of theory) of O-benzoyl-(4-chloro-phenoxy)-acetamide oxime are obtained.

M.p.: 149° C.

$^1$H-NMR (CDCl$_3$, δ, ppm): 4.75 (s, 2H, —CH$_2$—O—); 5.25 (br. s, 2H, —NH$_2$); 6.93; 7.26 (2d, 4H, arom. H; J=9.1 Hz); 7.43–8.07 (3m, 5H, arom. H)

The compounds of the formula (VI) which are listed in Table 3 below can be prepared analogously.

TABLE 3

Starting substances of the formula (VI)

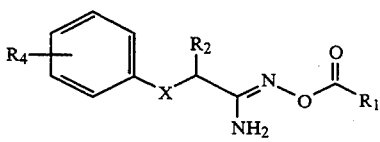

(VI)

| Example No. | X  | R$^1$         | R$^2$ | R$^4$    | Physical Data |
|-------------|----|---------------|-------|----------|---------------|
| VI-2        | O  | CH$_3$        | H     | 2,4-Cl$_2$ | 4.74; 5.20$^{a)}$ |
| VI-3        | O  | CH$_3$        | H     | 4-Cl     | 4.66; 5.13$^{a)}$ |
| VI-4        | O  | —(CH$_2$)$_2$—Cl | H     | 4-Cl     | 4.53; 6.95$^{b)}$ |
| VI-5        | O  | 4-F-phenyl    | H     | 4-Cl     | 4.75; 5.23$^{a)}$ |
| VI-6        | O  | fur-2-yl      | H     | H        | 4.77; 5.30$^{a)}$ |
| VI-7        | NH | CH$_3$        | H     | 4-Cl     | 3.91; 5.22$^{a)}$ |
| VI-8        | S  | thien-2-yl    | H     | 4-Cl     | 3.77; 5.22$^{a)}$ |

$^{a)}$ $^1$H-NMR (CDCl$_3$, δ, ppm)
$^{b)}$ $^1$H-NMR (DMSO-d$_6$, δ, ppm) in each case singlets for

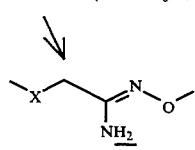

Example for the preparation of the 5-substituted 3-halogenoalkyl-1,2,4-oxadiazoles, which are employed as precursors (cf. DE-OS (German Published Specification) 2,406,786).

Example (VII-1)

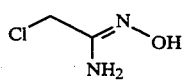

106.0 g (1.0 mol) of sodium carbonate are added, in portions, to a solution of 69.5 g (1.0 mol) of hydroxylamine hydrochloride in 250 ml of water and 75.5 g (1.0 mol) of chloroacetonitrile; during this process, the reaction temperature should not exceed 30° C. The reaction mixture is stirred for another 15 minutes at 30° C. and then subsequently extracted using ether. The organic phases are dried over magnesium sulphate, concentrated in vacuo and stirred with diisopropyl ether. 54.6 g (50.3% of theory) of chloroacetamide oxime are obtained.

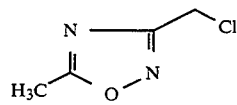

54.6 g (0.5 mol) of chloroacetamide oxime are introduced into 96 ml of acetic anhydride and the mixture is stirred for 2 hours at 120° to 130° C. The entire batch is subsequently concentrated in vacuo, neutralised using sodium hydrogen carbonate and extracted using ethyl acetate.

The organic phase is dried over magnesium sulphate, the solvent is distilled off, and the oily residue is distilled in vacuo. 27.3 g (41.2% of theory) of 3-chloromethyl-5-methyl-1,2,4-oxadiazole are obtained.

B.p.$_{12mbar}$: 60° to 75° C.

$^1$H-NMR (CDCl$_3$, δ, ppm): 2.63 (s, 3H, —CH$_3$); 4.59 (s, 2H, —CH$_2$—Cl)

Example for the preparation of the substituted acetonitriles, which are employed as precursors (cf. I. Cervena et al. Collect. Czech. Chem. Commun. 46(1981) 5, p. 1188–1198)

Example (IX-1)

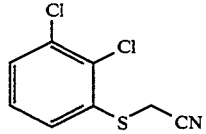

15.0 g (83.8 mmol) of 2,3-dichloro-thiophenol are introduced into 50 ml of absolute methanol, 4.5 g (83.8 mmol) of sodium methanolate are added in portions, with cooling, and the mixture is stirred for 15 minutes at room temperature. 6.3 g (83.8 mmol) of chloroacetonitrile are subsequently added dropwise, and the mixture is stirred for 2 hours at room temperature and for a further 5 hours at reflux temperature. The entire batch is then filtered while hot and concentrated in vacuo. 10.8 g (59.1% of theory) of 2,3-dichloro-phenylthioacetonitrile are obtained.

$^1$H-NMR (DMSO-d$_6$, δ, ppm): 4.44 (s, 2H, —CH$_2$—S—); 6.87–7.59 (m, 3H, arom. H)

The compounds of the formula (IX) which are listed in Table 4 below can be prepared analogously.

TABLE 4

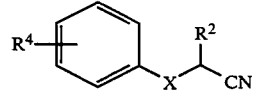

(IX)

| Example No. | X    | R$^2$ | R$^4$         | Physical Data |
|-------------|------|-------|---------------|---------------|
| IX-2        | O    | H     | 2-CH$_3$      | 5.17$^{b)}$   |
| IX-3        | O    | H     | 3-CH$_3$      | 4.68$^{a)}$   |
| IX-4        | O    | H     | 4-CH$_3$      | 5.11$^{b)}$   |
| IX-5        | O    | H     | 4-t-C$_4$H$_9$ | 4.73$^{a)}$   |
| IX-6        | O    | H     | 2-Cl          | 5.31$^{b)}$   |
| IX-7        | O    | H     | 3-Cl          | 5.23$^{b)}$   |
| IX-8        | O    | H     | 3,4-Cl$_2$    | 5.24$^{b)}$   |
| IX-9        | O    | H     | 3-Cl,4-CF$_3$ | 5.44$^{b)}$   |
| IX-10       | O    | H     | 3-CF$_3$      | 5.33$^{b)}$   |
| IX-11       | NH   | H     | 4-CH$_3$      | 4.04$^{a)}$   |
| IX-12       | S    | H     | 3,4-(OCH$_3$)$_2$ | 4.10$^{b)}$ |
| IX-13       | S    | H     | 4-Cl          | 4.27$^{b)}$   |
| IX-14       | S    | H     | 2-F,3-Cl      | 3.63$^{b)}$   |
| IX-15       | SO$_2$ | H   | 4-CH$_3$      | 5.20$^{b)}$   |

TABLE 4-continued (IX)

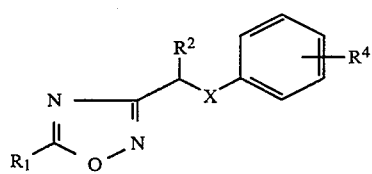

| Example No. | X | $R^2$ | $R^4$ | Physical Data |
|---|---|---|---|---|
| IX-16 | $SO_2$ | H | 4-Cl | 5.31[b] |

[a] $^1$H-NMR ($CDCl_3$, δ, ppm);
[b] $^1$H-NMR (DMSO-$d_6$, δ, ppm) in each case singlet for
—X—$CH_2$—

We claim:

1. A method of combating cestodes, trematodes and nematodes in a patient afflicted therewith which comprises administering to such patient an amount effective therefor of a substituted 1,2,4-oxadiazole of the formula I

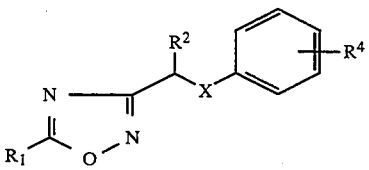

in which
$R^1$ represents hydrogen, $C_1$-$C_4$-alkyl which is optionally substituted by halogen, $C_1$-$C_4$-alkoxy, hydroxyl, amino, $C_1$-$C_4$-alkylamino, $C_1$-$C_4$-dialkylamino, cyclo-$C_3$-$C_7$-alkylamino, cyclo-substituted $C_3$-$C_7$-alkyl, phenyl, furyl, thienyl or pyridyl,
$R^2$ represents hydrogen and $C_1$-$C_4$-alkyl,
X represents O, S, SO, $SO_2$ and —N-$R^3$,
$R^3$ represents hydrogen, $C_1$-$C_4$-alkyl, $C_1$-$C_4$-alkylcarbonyl, halogen-$C_1$-$C_4$-alkylcarbonyl,
$R^4$ represents identical or different radicals selected from the group consisting of hydrogen, halogen, cyano, nitro, isothiocyanato, amino, $C_1$-$C_4$-alkylamino, $C_1$-$C_4$-dialkylamino, $C_1$-$C_4$-trialkylammonium halide, trimethylammonium chloride or trimethylammonium iodide, sulphonylamino, hydroxyl, mercapto, $C_1$-$C_9$-alkyl, halogeno-$C_1$-$C_4$-alkyl, $C_1$-$C_4$-alkoxy or methylenedioxy or ethylenedioxy, each of which is optionally substituted by fluorine or chlorine, halogeno-$C_1$-$C_4$-alkoxy, $C_1$-$C_4$-alkylthio, $C_1$-$C_4$-halogenoalkylthio, $C_1$-$C_4$-alkylsulphinyl, $C_1$-$C_4$-halogenoalkylsulphinyl, $C_1$-$C_4$-alkylsulphonyl, $C_1$-$C_4$-halogenoalkylsulphonyl, methoxycarbonyl, ethoxycarbonyl, acetyl, propionyl and oxadiazolylmethyleneoxy which is substituted by one of the radicals indicated for $R^1$.

2. The method according to claim 1, in which
$R^1$ represents hydrogen, methyl, ethyl, isopropyl, sec. butyl, trichloromethyl or trifluoromethyl,
$R^2$ represents hydrogen or methyl,
X represents O, S, SO, $SO_2$ and —N-$R^3$,
$R^3$ represents hydrogen, acetyl, propionyl or trifluoroacetyl,
$R^4$ represents identical or different radicals selected from the group consisting of fluorine, chlorine, bromine, methylamino, ethylamino, dimethylamino, trimethylammonium bromide, trimethylammonium chloride, trimethylammonium iodide, trifluoromethyl, methoxy, ethoxy, trifluoromethoxy, fluorochloroethoxy, methylthio, trifluoromethylthio, fluorochloromethylthio, methylsulphinyl, trifluoromethylsulphinyl, methylsulphonyl, trifluoromethylsulphonyl, and 3-(1,2,4-oxadiazolyl)-methyleneoxy, which is substituted by one of the radicals given under $R^1$.

3. A substituted 1,2,4-oxadiazole derivatives of the formula (I)

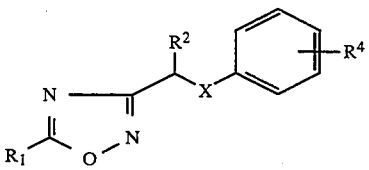

in which
$R^1$ represents hydrogen, $C_1$-$C_4$-alkyl which is optionally substituted by halogen, phenyl, furyl, thienyl or pyridyl,
$R^2$ represents hydrogen and $C_1$-$C_4$-alkyl,
X, in the event that $R^2$ represents $C_{1-4}$-alkyl, represents O, S, SO, $SO_2$ and N-$R^3$,
X, in the event that $R^2$ represents hydrogen, represents O, SO, $SO_2$ and N-$R^3$,
$R^3$ represents $C_1$-$C_4$-alkyl,
$R^4$ represents identical or different radicals selected from the group consisting of hydrogen, halogen, cyano, nitro, isothiocyanato, amino, $C_1$-$C_4$-alkylamino, $C_1$-$C_4$-dialkylamino, $C_1$-$C_4$-trialkylammonium halide, sulphonylamino, hydroxyl, mercapto, $C_1$-$C_9$-alkyl, halogeno-$C_1$-$C_4$-alkyl, $C_1$-$C_4$-alkoxy or methylenedioxy or ethylenedioxy, each of which is optionally substituted by fluorine or chlorine, halogeno-$C_1$-$C_4$-alkoxy, $C_1$-$C_4$-alkylthio, $C_1$-$C_4$-halogenoalkylthio, $C_1$-$C_4$-alkylsulphinyl, $C_1$-$C_4$-halogenoalkylsulphinyl, $C_1$-$C_4$-alkylsulphonyl, $C_1$-$C_4$-halogenoalkylsulphonyl, methoxycarbonyl, ethoxycarbonyl, acetyl, propionyl and oxadiazolylmethyleneoxy which is substituted by one of the radicals indicated for $R^1$.

4. An endoparasiticidal agent comprising an endoparasiticidally effective amount of at least one substituted 1,2,4-oxadiazole derivative of the formula (I) according to claim 3 and a diluent.

* * * * *

UNITED STATES PATENT AND TRADEMARK OFFICE
CERTIFICATE OF CORRECTION

PATENT NO. : 5,428,047
DATED : June 27, 1995
INVENTOR(S) : Jeschke, et al.

It is certified that error appears in the above-indentified patent and that said Letters Patent is hereby corrected as shown below:

Col. 27, line 27  Delete " 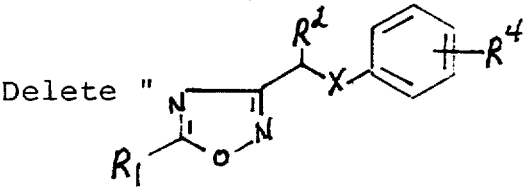 " and substitute -- 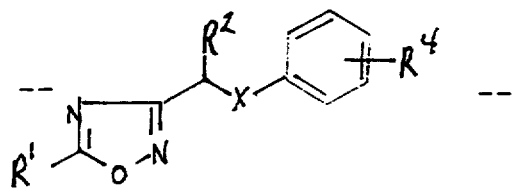 --

Col. 27, lines 34-35  Delete " cyclo-substituted $C_3$-$C_7$-alkyl " and substitute -- cyclo-$C_3$-$C_7$-alkyl --

Col. 28, line 27  Delete " 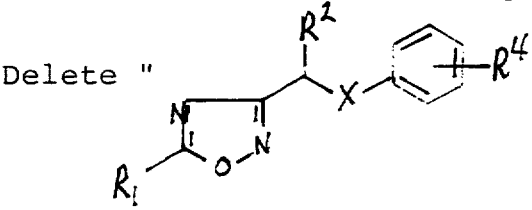 " and

UNITED STATES PATENT AND TRADEMARK OFFICE
CERTIFICATE OF CORRECTION

PATENT NO. : 5,428,047
DATED : June 27, 1995
INVENTOR(S) : Jeschke, et al.

It is certified that error appears in the above-indentified patent and that said Letters Patent is hereby corrected as shown below:

Col. 28, line 27    substitute  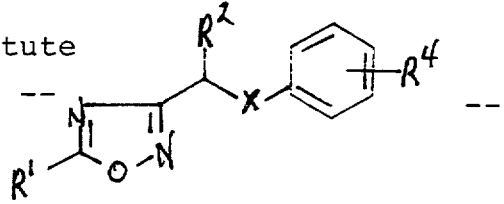
Cont'd

Signed and Sealed this

Seventeenth Day of October, 1995

BRUCE LEHMAN

Attesting Officer    Commissioner of Patents and Trademarks